(12) United States Patent
Bodenhamer (10) Patent No.: US 6,841,392 B2
(45) Date of Patent: Jan. 11, 2005

(54) METHOD AND APPARATUS FOR SELECTIVE BIOLOGICAL MATERIAL DETECTION

(75) Inventor: William T. Bodenhamer, Jupiter, FL (US)

(73) Assignee: Toxin Alert, Inc., Ontario (CA)

( * ) Notice: Subject to any disclaimer, the term of this patent is extended or adjusted under 35 U.S.C. 154(b) by 136 days.

(21) Appl. No.: 09/930,563

(22) Filed: Aug. 15, 2001

(65) Prior Publication Data

US 2002/0045200 A1 Apr. 18, 2002

Related U.S. Application Data

(63) Continuation-in-part of application No. 09/550,779, filed on Apr. 17, 2000, now Pat. No. 6,379,908, which is a continuation-in-part of application No. 09/218,827, filed on Dec. 22, 1998, now Pat. No. 6,051,388.

(51) Int. Cl.$^7$ .......................................... G01N 33/543
(52) U.S. Cl. .................. 436/518; 435/7.1; 435/7.93; 435/287.7; 435/287.9; 435/805; 435/810; 435/970; 436/514; 436/530; 436/531; 436/537; 436/805
(58) Field of Search .................. 435/7.1, 7.93, 435/287.7, 287.9, 805, 810, 970; 436/514, 518, 530, 531, 537, 805

(56) References Cited

U.S. PATENT DOCUMENTS

| | | |
|---|---|---|
| 2,485,566 A | 10/1949 | Clark |
| 3,067,015 A | 12/1962 | Lawdermilt |
| 4,285,697 A | 8/1981 | Neary |
| 4,746,616 A | 5/1988 | Honigs et al. |
| 4,757,002 A | 7/1988 | Joo |
| 4,870,005 A | 9/1989 | Akiyoshi et al. |
| 4,966,856 A | 10/1990 | Ito et al. |
| 5,053,339 A | 10/1991 | Patel |
| 5,266,460 A | 11/1993 | Sudo et al. |
| 5,306,466 A | 4/1994 | Goldsmith |
| 5,869,341 A | 2/1999 | Woodaman |
| 5,874,165 A | 2/1999 | Drumheller |
| 6,020,047 A | 2/2000 | Everhart |
| 6,051,388 A | 4/2000 | Bodenhamer |
| 6,270,724 B1 | 8/2001 | Woodaman |

FOREIGN PATENT DOCUMENTS

| | | |
|---|---|---|
| EP | 0 313 858 | 5/1989 |
| EP | 0 327 918 | 8/1989 |
| EP | 0 699 304 B1 | 12/1999 |
| WO | WO 94/27144 | 11/1994 |

Primary Examiner—Christopher L. Chin
(74) Attorney, Agent, or Firm—McHale & Slavin, P.A.

(57) ABSTRACT

The present invention relates to bioassay materials useful for the detection of toxic substances and, more particularly, to packaging materials for food and other products, along with methods for their manufacture and use. The invention provides a unique composite material capable of detecting and identifying multiple biological materials within a single package. The biological material identification system is designed for incorporation into existing types of flexible packaging material such as polyvinylchloride or polyolefin films, and its introduction into the existing packaging infrastructure will require little or no change to present systems or procedures.

20 Claims, 8 Drawing Sheets

FIG. 1

Note: the approximate thickness of the antibody sandwich is 100 microns

SINGLE LIGAND ASSAY CONSTRUCTION

FIG. 3
SINGLE LIGAND ASSAY OPERATION  Step 1

FIG. 4
TOXIN QUANTIFICATION BY SCAVANGER SYSTEM

Scavenger Step 2

Scavenger Step 3 after 30 minutes
distinct pattern after 72 hours
dark distinct pattern

Checkerboard Dot-Spot Application of RaMBP on a Polyvinychloride Surface and Detection by GaR$^{HRP}$

GENERAL LAYOUT APPLICATION MACHINERY

METHOD AND APPARATUS FOR SELECTIVE BIOLOGICAL MATERIAL DETECTION

REFERENCE TO RELATED APPLICATIONS

This application is a continuation-in-part of Ser. No. 09/550,779, filed on Apr. 17, 2000, now U.S. Pat. No. 6,379,908, which is a continuation-in-part of Ser. No. 09/218,827, filed on Dec. 22, 1998 and now U.S. Pat. No. 6,051,388, having an issue date of Apr. 18, 2000, the contents of which are herein incorporated by reference.

FIELD OF THE INVENTION

This invention relates to the detection of pathogenic microorganisms, or biological materials, and more particularly relates to a composite bioassay material useful for the detection of particular toxic substances, its method of manufacture and method of use, wherein the composite material is particularly useful for food packaging and the like, and is capable of simultaneously detecting and identifying a multiplicity of such biological materials.

BACKGROUND OF THE INVENTION

Although considerable effort and expense have been put forth in an effort to control food borne pathogenic microorganisms, there nevertheless exist significant safety problems in the supply of packaged food. For example, numerous outbreaks of food poisoning brought about by foodstuffs contaminated with strains of the E-Coli, Campylobacter, Listeria, Cyclospora and Salmonella microorganisms have caused illness and even death, not to mention a tremendous loss of revenue for food producers. These and other microorganisms can inadvertently taint food, even when reasonably careful food handling procedures are followed. The possibility of accidental contamination, for example by temperature abuse, in and of itself, is enough to warrant incorporation of safe and effective biological material diagnosis and detection procedures. Further complicating the situation is the very real possibility that a terrorist organization might target either the food or water supply of a municipality or even a nation itself, by attempting to include a pathogenic microorganism or toxic contaminant capable of causing widespread illness or even death. If, by accident or design, the food supply of a particular population were to be contaminated, it is not only imperative that the population be alerted to the contamination, but it is further necessary that the particular contaminant be quickly and precisely pinpointed so that appropriate countermeasures may be taken.

Thus, if it were possible to readily substitute standard packaging materials with a flexible material capable of 1) quickly and easily detecting the presence, and 2) indicating the particular identity of a variety of pathogenic biological materials, a long felt need would be satisfied.

DESCRIPTION OF THE PRIOR ART

The Berkeley Lab Research News of Dec. 10, 1996, in an article entitle "New Sensor Provides First Instant Test for Toxic E. Coli Organism" reports on the work of Stevens and Cheng to develop sensors capable of detecting E. Coli strain 0157:H7. A color change from blue to red instantaneously signals the presence of the virulent E. Coli 0157:H7 microorganism. Prior art required test sampling and a 24 hour culture period in order to determine the presence of the E. Coli microorganism, requiring the use of a variety of diagnostic tools including dyes and microscopes. An alternative technique, involving the use of polymerase chain reaction technology, multiplies the amount of DNA present in a sample until it reaches a detectable level. This test requires several hours before results can be obtained. The Berkeley sensor is inexpensive and may be placed on a variety of materials such as plastic, paper, or glass, e.g. within a bottle cap or container lid. Multiple copies of a single molecule are fabricated into a thin film which has a two part composite structure. The surface binds the biological material while the backbone underlying the surface is the color-changing signaling system.

The Berkeley researchers do not teach the concept of incorporating any means for self-detection within food packaging, nor do they contemplate the inclusion of multiple means capable of both detecting and identifying the source of pathogenic contamination to a technically untrained end user, e.g. the food purchaser or consumer.

Wang et al, in an article entitled "An immune-capturing and concentrating procedure for Escherichia coli 0157:H7 and its detection by epifluorescence microscopy" published in Food Microbiology, 1998, Vol. 15 discloses the capture of E. coli on a polyvinylchloride sheet coated with polyclonal anti-E. coli 0157:H7 antibody and stained with fluorescein-labeled anti-E. coli 0157:H7. After being scraped from the PVC surface, the cells were subjected to epifluorescence microscopy for determining presence and concentration. The reference fails to teach or suggest the concept of incorporating any means for self-detection within food packaging, nor does it contemplate the inclusion of multiple means capable of both detecting and identifying the source of pathogenic contamination to a technically untrained end user, e.g. the food purchaser or consumer, and especially fails to disclose such detection without the use of specialized detection techniques and equipment.

U.S. Pat. No. 5,776,672 discloses a single stranded nucleic acid probe having a base sequence complementary to the gene to be detected which is immobilized onto the surface of an optical fiber and then reacted with the gene sample denatured to a single stranded form. The nucleic acid probe, hybridized with the gene is detected by electrochemical or optical detection methodology. In contrast to the instantly disclosed invention, this reference does not suggest the immobilization of the probe onto a flexible polyvinylchloride or polyolefin film, nor does it suggest the utilization of gelcoats having varying porosities to act as a control or limiting agent with respect to the migration of antibodies or microbial material through the bioassay test material, or to serve as a medium for enhancement of the growth of the microbial material.

U.S. Pat. No. 5,756,291 discloses a method of identifying oligomer sequences. The method generates aptamers which are capable of binding to serum factors and all surface molecules. Complexation of the target molecules with a mixture of nucleotides occurs under conditions wherein a complex is formed with the specific binding sequences but not with the other members of the oligonucleotide mixture. The reference fails to suggest the immobilization of the aptamers upon a flexible polyvinylchloride or polyolefin base material, nor does it suggest the use of a protective gelcoat layer which acts as a means to selectively control the migration of antibodies and antigens, or to serve as a medium for enhancement of the growth of microbial material.

SUMMARY OF THE INVENTION

The present invention relates to packaging materials for food and other products, along with methods for their manufacture and use. The presence of undesirable biological materials in the packaged material is readily ascertained by the consumer, merchant, regulator, etc. under ordinary conditions and without the use of special equipment. A multiplicity of biological materials threaten our food supply. The present invention provides a unique composite material capable of detecting and identifying multiple biological materials within a single package. The biological material identification system is designed for incorporation into existing types of flexible packaging material such as polyvinylchloride and polyolefin films, and its introduction into the existing packaging infrastructure will require little or no change to present systems or procedures. Thus, the widespread inclusion of the biological material detecting system of the instant invention will be both efficient and economical.

In one embodiment of the invention the biological material detecting system prints a pattern containing several antibodies or aptamers, derived from plant or animal origins, onto a packaging material which is usually a type of polymeric film, preferably a polyvinylchloride or polyolefin film and most preferably a polyethylene film which has undergone a surface treatment, e.g. corona discharge to enhance the film's ability to immobilize the antibodies upon its surface. The agents are protected by a special abrasion resistant gel coat in which the porosity is tailored to control the ability of certain antibodies, toxic substances, etc. to migrate therethrough. Each antibody is specific to a particular biological material and is printed having a distinctive icon shape. The detection system may contain any number of antibodies capable of detecting a variety of common toxic food microbes; although any number of microbes may be identified via the inventive concept taught herein, for the purpose of this description, the microbes of interest will be limited to *E. Coli, Salmonella, Listeria* and *Cyclospora*.

An important feature of the biological material detection system is its all-encompassing presence around and upon the product being packaged. Since the biological material detecting system is designed as an integral part of 100% of the packaging material and covers all surfaces as utilized, there is no part of the packaged product which can be exposed to undetected microbes. In the past, the use of single location or in situ detectors have left a majority of the area around and upon the packaged product exposed to undetected microbes. This greatly increased the chance that a spoiled or tainted product might be inadvertently consumed before the toxic agent had spread to the location of the in situ detector. The biological material detection system of the present invention avoids this problem by providing a plurality of individual detectors per unit area which are effective to insure positive detection of any pathogenic microorganisms within the product being tested. In order to be effective a particular degree of sensitivity is required, e.g. the detecting system must be capable of positively identifying one microbial cell in a 25 gram meat sample. In a preferred embodiment, four detectors per square inch of packaging material surface have been utilized, and in a most preferred embodiment nine or more detectors per square inch are incorporated upon the film's surface.

By use of the biological material detection system of the present invention a packager or processor can independently determine the multiplicity and identity of those biological materials against which the packaged product is to be protected. Although it is envisioned that the large majority of biological material detection treated packaging will be generic to approximately four of the most common microbes, the system will nevertheless allow each user to customize the protection offered to the public.

The biological material detecting system will not merely detect the presence of biological materials, it will also identify the particular biological materials located in a packaged product. This unique feature allows for the immediate identification of each particular biological material present since the antibodies are specific to a detector having a definitive icon shape or other identifying characteristic. Although the end use consumer is primarily interested in whether a food product is, or is not, contaminated per se, the ability to detect and identify the particular biological material immediately is of immeasurable value to merchants, processors, regulators and health officials. The ability to immediately identify a toxic material will lead to greatly reduced response times to health threats that might be caused by the biological material and will also enhance the ability for authorities to locate the source of the problem. The biological material detecting system of the present invention exhibits an active shelf life in excess of 1 year under normal operating conditions. This enhances the use of a biological material detection system on products which are intended to be stored for long periods of time. If these products are stored so as to be ready for immediate use in some time of emergency, then it is extremely beneficial to definitely be able to determine the safety of the product at the time that it is to be used.

One particularly important feature of the biological material detecting system of the instant invention is its ability to quantitatively sensitize the reagents so as to visually identify only those biological materials which have reached a predetermined concentration or threshold level which is deemed to be harmful to humans.

For example, almost all poultry meat contain traces of the salmonella bacteria. In most cases, the salmonella levels have not reached a harmful level of concentration. The biological material detecting reagents are designed to visually report only those instances where the level of concentration of biological materials are deemed harmful by health regulatory bodies.

The method of production of the biological material detecting system is designed to be easily incorporated within the packaging infrastructure of existing systems without disruption of the systems or the procedures under which they are operating. The biological material detecting system can be incorporated onto packaging films which are produced by the packager, or those which are supplied by a film manufacturer. The apparatus necessary for applying the biological material detecting system may be easily located at the beginning of any continuous process such as printing or laminating and will operate as an integral part of an existing system.

The biological material detecting system of the instant invention represents an entirely new packaging material which is designed to inform the consumer of the presence of certain biological materials or pathogens present in food stuffs or other materials packaged within the detecting system. The system is designed so that the presence of a biological material is presented to the consumer in a distinct, unmistakable manner which is easily visible to the naked eye.

Recent outbreaks of *E. Coli* and other health hazards have presented serious problems to the general population and have raised concerns regarding the safety of the food supply.

It is an objective of the present invention to provide a biological material detecting system for protecting the consumer by detecting and unmistakably presenting to the untrained eye visual icons on the packaging material which signify the presence of a number of pathogens in the food stuff or other materials which are at a level harmful to humans.

It is another objective of the instant invention to provide a bioassay material wherein an antigen detecting antibody system is immobilized upon the surface of a flexible polyolefin film.

It is still another objective of the instant invention to provide a bioassay material wherein an antigen detecting antibody system is immobilized upon the surface of a flexible polyvinylchloride film.

It is a further objective of the invention to provide a biological material detecting system which is so similar in appearance and utilization that its use, in lieu of traditional packaging materials, is not apparent to the food processor or other packagers.

A still further objective of the present invention is to provide a biological material detecting system which is cost effective when compared to traditional packaging materials.

It is still another objective of the present invention to provide a biological assay material for protecting the consumer by detecting and unmistakably presenting to the untrained eye one or more visual icons on a packaging material which signify the presence or absence of a particular toxic substance.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DESCRIPTION OF THE PREFERRED EMBODIMENTS

Figure 1:
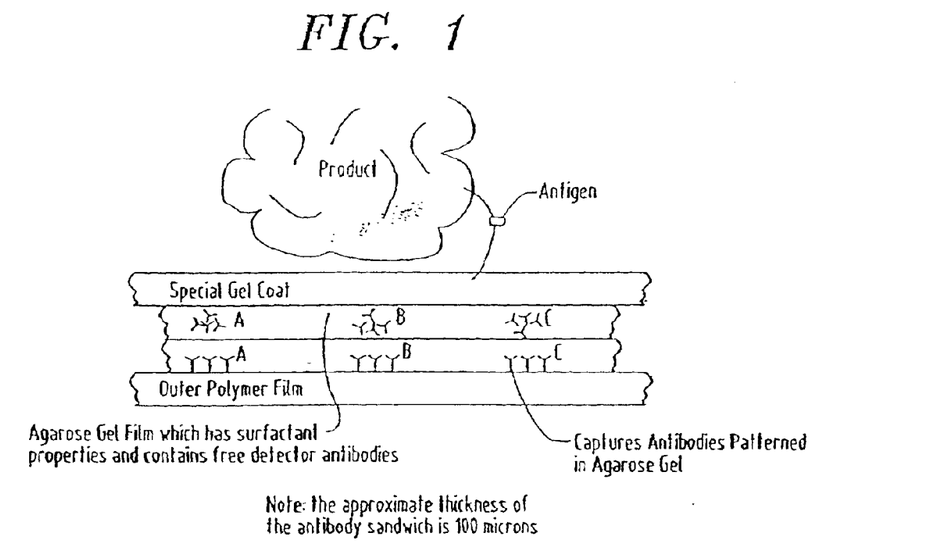
FIG. 1 is a cross-sectional interpretation of an antibody sandwich immunoassay device.
Figure 7:
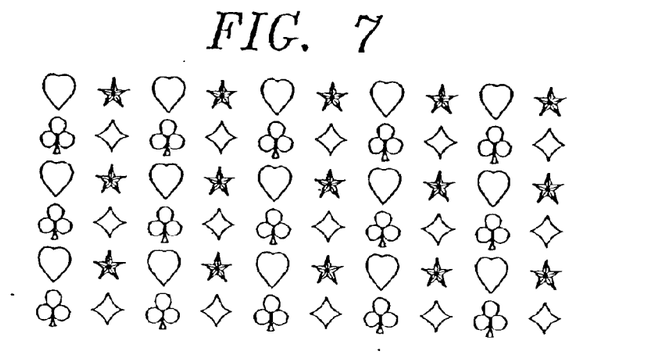
FIG. 7 is a planar view of an example of icon placement and printing.
Figure 7A:
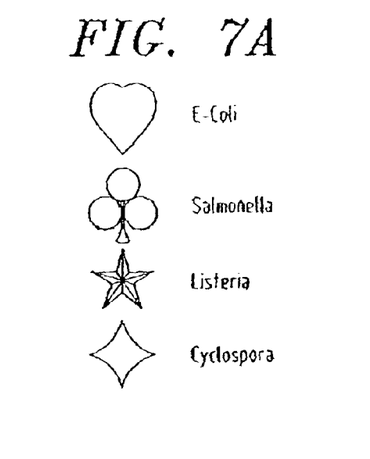
FIG. 7A is an example of a typical code of identification applied to the icon pattern.

Referring now to FIG. 1, the detection and identification of various biological materials in packaged foods or other products is accomplished by the use of antibodies which are specific to the biological material being sought. Specific antibodies, defined as capture antibodies, are biologically active ligands characterized by their ability to recognize an epitope of the particular toxic substance being tested. These capture antibodies are selected from such materials as antibodies, aptamers, single stranded nucleic acid probes, lipids, natural receptors, lectins, carbohydrates and proteins. In one embodiment of the invention, the capture antibodies are arranged with unique icon shapes and in particular patterns. The capture antibodies are immobilized to the polymer film. An agarose gel coat containing detector antibodies is printed in register above the capture antibodies. A protective gel coat completes the construction of the packaging material. The gel coat constituting the inner layer, e.g. that layer which is next to the packaged product, is a special type of gel coat or an equivalent thereto which has sufficient porosity to allow toxic molecules, known as antigens, to migrate through it to an antibody "sandwich" laminated between the polymer film and the gel coat. The special gel coat has sufficient abrasion resistance to prevent exposure of the reagents to the product. The special gel coat useful in the invention is a readily available coating commonly utilized in the food industry to coat candies and the like, e.g. coated chocolates to prevent them from melting on one's hands. Migration of antigens is driven by capillary action and normally reaches a state of equilibrium within a 72 hour time period. In a particularly preferred embodiment, when operating within a temperature range of 4–25 degrees Celsius, an initial positive reading can be obtained within 30 minutes, and the test continues to yield results for about 72 hours. Upon migrating through the special gel coat the antigen enters an agarose gel film which has surfactant properties, contains free detector antibodies, and also contains one or more ingredients designed to enhance the growth of microbial materials, e.g. nutrients such as sorbitol, NOVOBIOCIN, CEFIXIME and TELLURITE which increase the growth rate and ease isolation of *E. Coli* 0157H. If the antigen encounters a species of antibody which is specific to an epitope thereof, it will then bind to it forming a detector/antibody complex. Once bound thereto, the bound antigen/antibody complex becomes too large to migrate back through the special gel coat due to its inherent fine porous structure. This insures that pathogenic material can not migrate back into the product being tested. Continuing pressure toward equilibrium from capillarity will tend to move the antigen, with its bound antibody, through a second gel coat layer and into an area of the flexible polyvinylchloride or polyolefin film containing corresponding species of immobilized capture antibodies. The layer of immobilized antibodies is attached to the outer polymer film in predetermined patterns of simple icons, as best seen in FIGS. 7, 7A. When the particular species of bound antigen encounters a particular corresponding species of immobilized antibody specific to a separate and distinct epitope thereof, further binding occurs. Upon the antigen binding to the two antibodies, a distinct icon shape emerges on the outer film at the point of binding, thereby providing a visual indicator.

While it is theoretically possible to detect an unlimited number of pathogens present in a packaged product, then to present this information in a very clear and unmistakable manner to an untrained consumer, as a practical matter there are limits to the amount of information which can be developed and presented in the biological material detecting system. Some of the limiting factors are cost, available surface area for display of information, complexity, and other considerations. Thus, for illustrative purposes only, the biological material detecting system as exemplified herein utilizes four separate pairs of antibodies, as set forth in FIGS. 7 and 7A. This is in no way meant to suggest a limit on the number of antibodies that can be utilized in a single biological material detecting system.

As demonstrated in FIGS. 7 and 7A, the invention is exemplified with reference to detection of the following four microbes:
1. *E-Coli;*
2. *Salmonella;*
3. *Listeria;* and
4. *Cyclospora.*

To each of the four microbes, a particular icon shape is assigned. Although there are infinite numbers of icons which might be used including letters, numbers, or even words, we have chosen simple identifiers for the purpose of demonstration. As an initial step in the construction of the biological material detecting system, the outer polymer film or base layer undergoes a printing process in which a pattern of the four icons, wherein each icon utilizes a specific species of immobilized capture antibody, is applied thereto. Corresponding species of free antibodies, known as detector antibodies, which are biologically active ligands characterized by their ability to recognize a different epitope of the same particular toxic substance being tested for, and suspended in an agarose gel solution containing a surfactant and a nutrient, are printed in registration with the immobilized antibodies so as to be in overlying and juxtaposed relationship thereto, and are then dried. Lastly, a second gel coat having a degree of porosity sufficient to prevent passage of the detector antibodies is laminated to the preparation.

Although the detection of biological materials through the use of antibodies is well known, there are several new and novel aspects to the application of antibody science which are set forth in the development of the biological material detecting system of the present invention.

Among these are: 1) the use of multiple antibodies to detect multiple biological materials in individual packages; 2) the use of a distinctive icon or other shape to not only detect, but visually identify the biological materials to the consumer, vendor, regulator, etc.; 3) insuring that detection and identification of the biological materials is accomplished in a timely manner in each particular application by judiciously controlling the porosity of the gel coat, thereby controlling the lapse rate of the reaction through the strength of capillary action; 4) inclusion of additives within the special gel coat to enhance the levels of microbes present; 5) incorporating the biological material detecting system of the instant invention within the existing packaging industry infrastructure; and 6) providing a bioassay material and methods for its production and use which immobilizes the antibodies onto the surface of a flexible polyvinylchloride or polyolefin, e.g. a polyethylene, a surface treated polyethylene, a polypropylene, a surface treated polypropylene or mixture thereof.

The embodiment discussed above is based upon a sandwich immunoassay as depicted in FIG. 1, which measures specific microbes, wherein the particular toxic substance is one or more members selected from the group consisting of a particular microorganism or species thereof, biological materials containing the genetic characteristics of said particular microorganism, and mutations thereof. In a particular embodiment, the toxic substance is selected from the group consisting of microorganisms, nucleic acids, proteins, integral components of microorganisms and combinations thereof.

It should also be understood that the invention will function by direct measurement of microbes with certain types of antibodies, selected from the group consisting of an antibody, a single stranded nucleic acid probe, an aptamer, a lipid, a natural receptor, a lectin, a carbohydrate and a protein. The biological materials may also be measured by non-immunological methods in particular using labeled molecules, such as aptamers, which have a high affinity for the biological materials.

The invention utilizes various types of detector antibodies, e.g. those conjugated with dyes to produce a visual cue, or alternatively, photoactive compounds capable of producing a visual cue in response to a particular type of light exposure, for example a scanning system which detects luminescent properties which are visualized upon binding of the antigen and antibody. In this method of construction biological materials are measured directly with a biologically active ligand, e.g. an antibody, aptamer, nucleic acid probe or the like, which induces a conformational change to produce a visual cue.

It is also understood that specific polymers may be incorporated into the invention and that when a biological material is bound to the surface it induces a molecular change in the polymer resulting in a distinctly colored icon.

Figure 2:
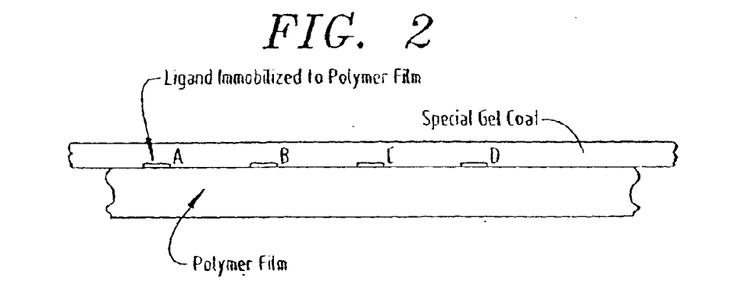
FIG. 2 is a cross-sectional interpretation of a single ligand assay.
Figure 2A:
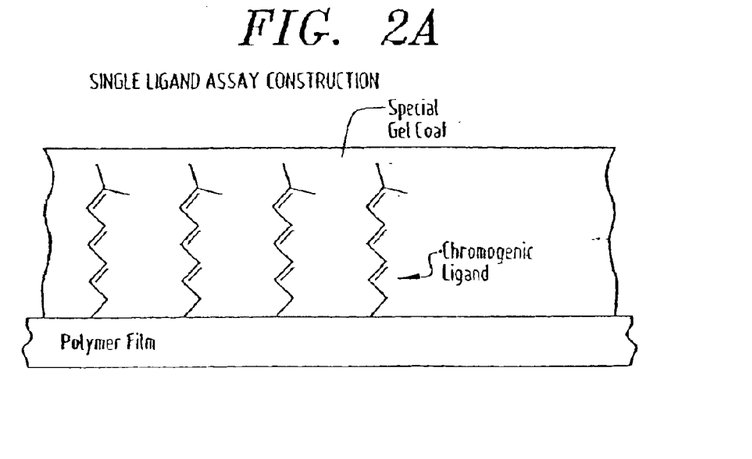
FIG. 2A is a cross-sectional interpretation of a single ligand assay including a chromogenic ligand.

Referring to FIGS. 2 and 2A, in an alternative embodiment, a sandwich-type of construction is not necessary. As depicted in FIGS. 2 and 2A, the provision of certain types of biologically active ligand, e.g. chromogenic ligands to which receptors are bound will permit the visual confirmation of binding of the antigen to the immobilized ligand.

Figure 3:
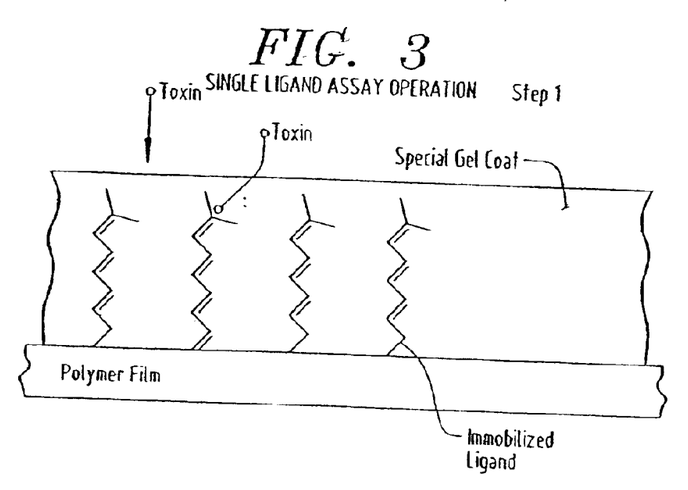
FIG. 3 is a diagrammatic representation showing the functioning of a single ligand assay.

As depicted in FIG. 3, a polymer film is provided and a biologically active ligand, preferably a chromogenic ligand, is immobilized to the polymer film. In the past, immobilized ligands were attached to rigid solid support matrices such as plastic, polystyrene beads, microtitre plates, latex beads, fibers, metal and glass surfaces and the like. The immobilized ligands have also been attached to flexible surfaces such as nitrocellulose or polyester sheets which were not transparent. Surprisingly, the inventor has discovered that it is possible to attach biologically active ligands to the surface of various flexible polymeric films, for example polyvinylchloride and polyolefins, e.g. a polyolefin sheet having appropriate properties of transparency and flexibility and that the composite functions as a biological sensor or assay material. After printing on the polymer film, the material goes through a drying step; subsequent to which a special gel coat or liquid film is applied as a protectant layer and the final product is then dried.

Illustrative of films which will function in the present invention is a film containing a structural polymer base having a treated surface and incorporating therein a fluorescing antibody receptor and finally a stabilized gel coat. These films may be untreated polyethylene or polyvinylchloride films which are amenable to antibody immobilization by various mechanisms, e.g. by adsorption. In a particular embodiment, the films may be first cleaned, e.g. by ultrasonication in an appropriate solvent, and subsequently dried. For example, the polymer sheet may be exposed to a fifteen minute ultrasonic treatment in a solvent such as methylene chloride, acetone, distilled water, or the like. In some cases, a series of solvent treatments are performed. Subsequently, the film is placed in a desiccating device and dried. Alternatively, these films may be created by first exposing the film to an electron discharge treatment at the surface thereof, then printing with a fluorescing antibody receptor. Subsequently, a drying or heating step may be utilized to treat the film to immobilize the receptor. Next, the film is washed to remove un-immobilized receptor; the film is then coated with a gel and finally dried.

Additional modifications to polyolefin films may be conducted to create the presence of functional groups, for example a polyethylene sheet may be halogenated by a free radical substitution mechanism, e.g. bromination, chlorosulfonation, chlorophosphorylation or the like. Furthermore, a halodialkylammonium salt in a sulfuric acid solution may be useful as a halogenating agent when enhanced surface selectivity is desirable.

Grafting techniques are also contemplated wherein hydrogen abstraction by transient free radicals or free radical equivalents generated in the vapor or gas phase is conducted. Grafting by various alternative means such as irradiation, various means of surface modification, polyolefin oxidation, acid etching, inclusion of chemical additive compounds to the polymer formulation which have the ability to modify the surface characteristics thereof, or equivalent techniques are all contemplated by this invention.

Additionally, the formation of oxygenated surface groups such as hydroxyl, carbonyl and carboxyl groups via a flame treatment surface modification technique is contemplated.

Further, functionalization without chain scission by carbene insertion chemistry is also contemplated as a means of polyolefin polymer modification.

Illustrative of the types of commercially available films which might be utilized are polyvinylchloride films and a straight polyethylene film with electron discharge treatment marketed under the trademark SCLAIR®. The electron discharge treatment, when utilized, renders the film much more susceptible to immobilization of the antibodies on its surface. Additional films which might be utilized are Nylon 66 films, for example DARTEK®, a coextrudable adhesive film such as BYNEL® and a blend of BYNEL® with polyethylene film.

Figure 4:
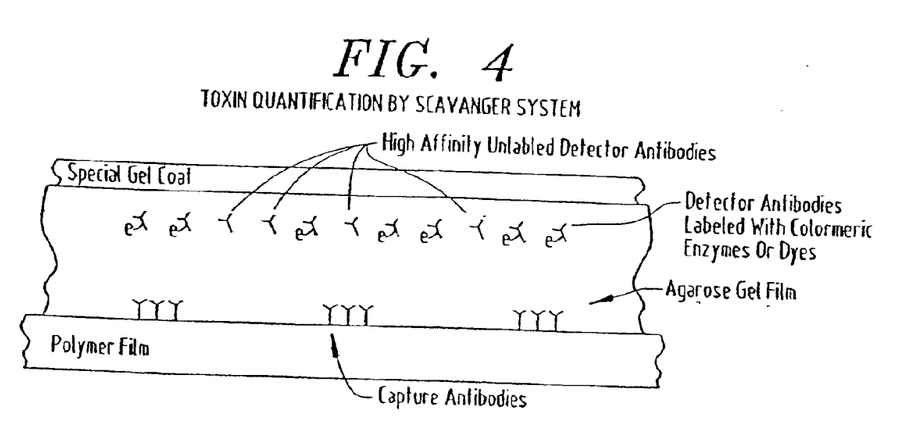
FIG. 4 is a cross-sectional interpretation of an antibody sandwich immunoassay including a scavenger system for microbial quantification.
Figure 5:
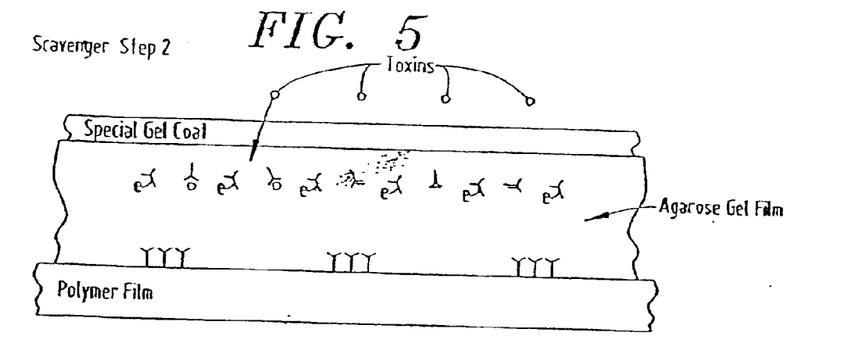
FIGS. 5 and 6 are a diagrammatic representation showing the functioning of a sandwich assay/scavenger system.
Figure 6:
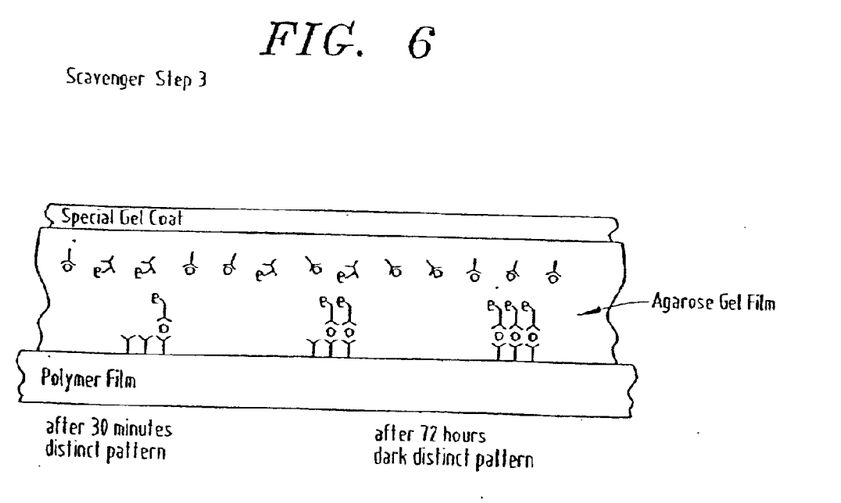

With reference to FIGS. 4–6, one of the most important features of the biological material detecting system is its ability to quantitatively sensitize the antibody or aptamer so as to visually identify only those biological materials that have reached a concentration level deemed harmful to humans. One means of providing this sensitization is by including a scavenger antibody which is a biologically active ligand characterized as having a higher affinity for the particular toxic substance than the capture antibody. The scavenger antibody is provided in a sufficient amount to bind with the particular toxic substance up to and including a specific threshold concentration. In this manner, the capture antibody will be prevented from binding with a detector antibody until the concentration of the particular biological material surpasses the specific threshold concentration. In this manner, the biological material detecting system visually reports only those instances where concentration levels are deemed harmful by health regulatory bodies.

Since the biological material detecting system as described herein can maintain its activity over long periods of time, e.g. up to 1 year, it is able to protect against contamination in products which have long shelf lives. Additionally, by reporting only toxic concentrations, it avoids "false positives" and, in some cases, can extend the useful life of the product.

Figure 9:
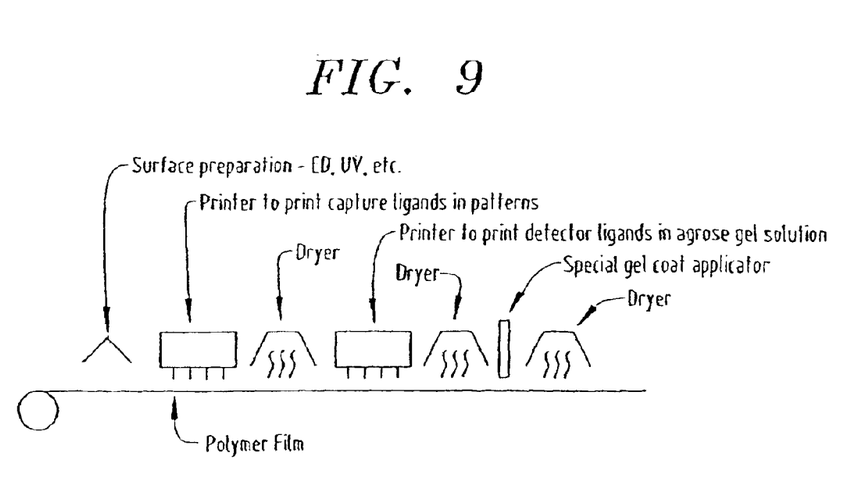
FIG. 9 is a block diagram of the apparatus illustrating the process steps for forming a sandwich assay.
Figure 10:
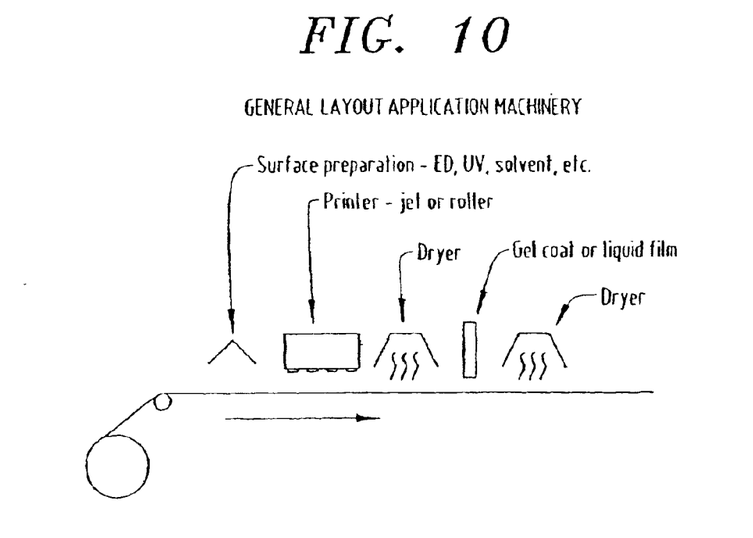
FIG. 10 is a block diagram of the apparatus illustrating the process steps for forming a single ligand assay.

Referring to FIGS. 9 and 10, the apparatus for producing the biological material detecting system is illustrated. These embodiments are essentially particular combinations of printers, coaters and dryers which will be used to place biologically active reagents upon a thin polymer film useful for packaging food stuffs and other products. These films will be further processed subsequent to application of the biological material detecting system by printing, laminating, or equivalent methods of fabrication. The machinery is designed so that it will transport and process very thin films at rather high speeds. Furthermore, the machinery is designed so that it can be utilized effectively as an additional processing step when added to continuous processing operations already in use at packaging material fabrication plants. The printing machinery is designed so that a minimum of four distinct biological active ligands in a hydrate solution can be printed in patterns in a precise registration on the polymer film. The printing may be accomplished by jet spray or roller application, or equivalent printing methods. Each print applicator is capable of printing a detailed icon no larger than ¼"×¼" in a minimum thickness. Patterning may be controlled by computer or roller calendaring. It is important to determine the appropriate viscosity of the solution to be applied so that successful printing, coating, and drying can be accomplished. After the printing step, the icons must be protected. This is accomplished by a final application of a thin special gel coat or a thin liquid film. By way of example, the liquid film may be an overprint food varnish. This step is accomplished by a 100% coating of the entire film or alternatively by selectively coating each icon such that a 10% overlap is coated beyond the icon in all directions. This coating step may be accomplished with sprays or rollers and the viscosity of the coating material must be optimized so as to provide adequate coverage. The biological material detecting system must be dried after printing and once again after coating. The drying is accomplished in a very rapid manner so as to enable high through put for the process. Various means of drying include the use of radiant heat, convected air and freeze drying. Care must be taken to avoid drying temperatures which will inactivate the biological reagents which have been applied. The polymer film which has been surface treated in the form of electron discharge, e.g. corona treatment, is most preferred. After preparation, the thin film is transported at relatively high speeds so that a wrinkle free surface is provided for printing, coating and rollup. Additionally, the apparatus provides a complete recovery system for the reagents which allows for total recovery of the agents and the volatile organic contaminants.

The invention will be further illustrated by way of the following examples:

EXAMPLE 1

Detection of Antibody on the Surface of a Thin Layer Polyvinylchloride Sheet:

Rabbit polyclonal IgG was diluted to a final concentration of 2.0 $\mu$g/ml in 0.1M carbonate ($Na_2CO_3$)-bicarbonate ($NaHCO_3$) buffer, pH 9.6.

Using a 2"×3" grid, 75 µL (150 ng) was applied to a sheet of polyvinylchloride at 1" intervals.

The antibody treated polyvinylchloride sheet was dried for 1.5 hours at a temperature of 37° C.

The dried sheet was then washed 3 times with a phosphate buffered saline solution at a pH of 7.4.

HRP conjugated goat anti-rabbit IgG (G$\alpha$R$^{HRP}$) was diluted to a concentration of 1:7000 in 1% casein, 0.1M potassium ferricyanide $K_3Fe(CN)_6$, 0.1% phosphate glass ($Na_{15}P_{13}O_{40}$—$Na_{20}P_{18}O_{55}$), at a pH of 7.4.

A precision pipette was used to apply 125 µL of diluted G$^{HRP}$ to the grid backed polyvinylchloride sheet at 1" intervals coinciding with the area covered by the previously coupled R$\alpha$G. The sheet was incubated at room temperature for 30 minutes.

The sheet was then washed 3 times with phosphate buffered saline at a pH of 7.4.

To the test areas, 125 µL of precipitating TMB enzyme substrate was added.

The sheet was incubated at room temperature until color development was complete.

Lastly, the sheet was washed 3 times with deionized water and allowed to air dry.

EXAMPLE 2
Full Sandwich Immunoassay on the Surface of a Thin Layer Polyvinylchloride Sheet:

Rabbit polyclonal IgG was diluted to a final concentration of 2.0 µg/ml in 0.1M carbonate ($Na_2CO_3$)-bicarbonate ($NaHCO_3$) buffer, pH 9.6.

A 13×9 cm piece of thin layered polyvinylchloride sheet was inserted into a BIO-RAD DOT-SPOT apparatus possessing 96 sample wells spaced at 1.0 cm intervals in a 12×8 well grid.

A 100 µL sample (1.0 µg) of rabbit polyclonal IgG was applied to each well of column 1 (8 wells total).

Antibody samples applied to columns 2–12 represented serial dilutions of the antibody ranging from 500 ng–0.5 ng.

The antibody treated polyvinylchloride sheet was dried overnight at 37° C.

The dried sheet was washed 3 times with phosphate buffered saline (PBS), pH 7.4.

The antigen was diluted to a final concentration of 1.0 µg/ml in TRIS buffered saline (TBS) with 1% casein, pH 7.4.

Applied to each well of the apparatus was 100 µL, representing 100 ng, of antigen, which was subsequently incubated at room temperature for 1 hour.

The polyvinylchloride sheet was washed 3 times with phosphate buffered saline (PBS), pH 7.4.

Detector mouse monoclonal antibody was diluted 1:625 with TBS containing 1% casein, 0.1M potassium ferricyanide $K_3Fe(Cn)_6$, and 0.1% phosphate glass ($Na_{15}P_{13}O_{40}$—$Na_{20}P_{18}O_{55}$), pH 7.4.

To each well of row 1, 100 µL of the 1:625 dilution of detector antibody solution was applied.

Detector samples of 100 µL applied to rows 2–7 represented serial dilutions of the antibody ranging from 1:1,250 to 1:80,000. Dilutions of detector antibody were incubated on the polyvinylchloride sheet for 1 hour at room temperature.

The polyvinylchloride sheet was washed 3 times with phosphate buffered saline (PBS), pH 7.4.

To each well of the DOT-SPOT apparatus, 100 µL of goat anti-mouse IgG$^{HRP}$ was added and allowed to incubate for one hour at room temperature.

The polyvinylchloride sheet was washed 3 times with phosphate buffered saline (PBS), pH 7.4.

To the test areas 100 µL of precipitating TMB enzyme substrate was added.

Figure 8:
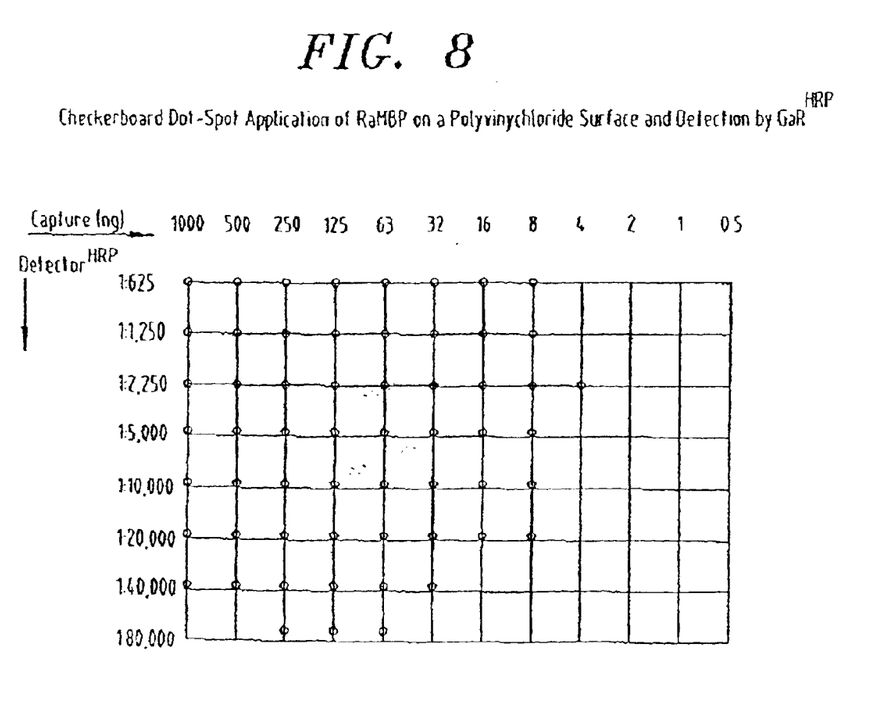
FIG. 8 is the result derived from EXAMPLE 2 and exemplifies capture sensitivity of a single ligand treated polyvinylchloride film.

The sheet was incubated at room temperature until color development was complete (see FIG. 8).

Lastly, the sheet was washed 3 times with deionized water and allowed to air dry.

Figure 11:
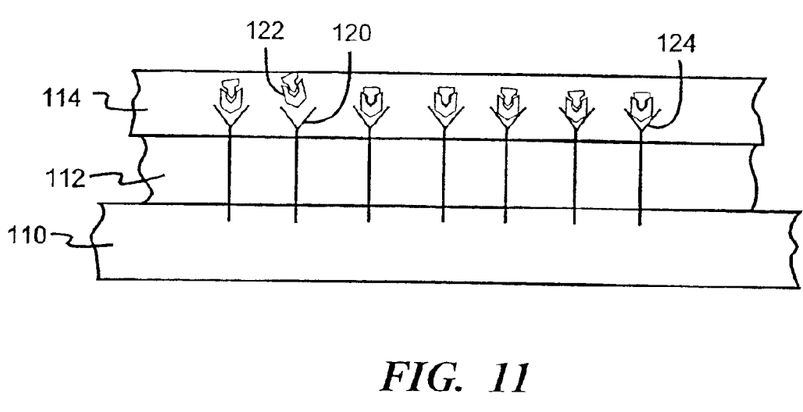
FIG. 11 is a diagrammatic representation showing first and second layers printed onto a base layer film.
Figure 13A:
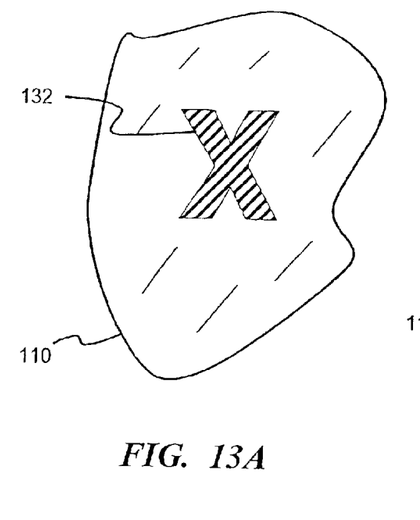
FIG. 13A illustrates a biological material assay in an icon shape visible on a film.

EXAMPLE 3
Half Sandwich Competitive Immunoassay on the Surface of a Thin Layer Polyvinylchloride Sheet:

In this example, the printing of an icon shape is employed, such as an "X" 132, illustrated in FIG. 13A. The icon is printed overlying a flexible film base layer 110, having two surfaces, prepared as previously described. A first layer 112 in an icon shape containing an overprint food varnish in combination with a capture antibody, referred to as a biologically active ligand, is printed over one surface of the base layer 110 to allow the immobilization of the biologically active ligand 120 to the surface of the film 110. A second layer 114, in register with the first 112, containing a buffer medium comprising a dye conjugated to a peptide 122, wherein the biologically active ligand has a degree of affinity for the peptide, is printed over the first layer 112 to allow contact for the peptide/dye conjugate 122 to bind to the immobilized ligand 120 (FIG. 11) forming a homogeneous conjugate blend 124. At this point, the area printed on the film appears colored. The dye chosen for this example is a food dye giving a blue coloration, and therefore a blue "X" 132 is visualized (FIG. 13A).

Figure 12:
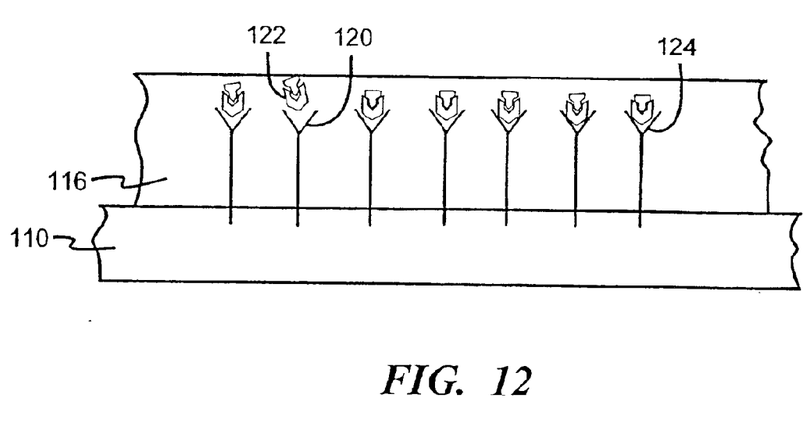
FIG. 12 is a diagrammatic representation showing a first layer printed onto a base layer film.

In a further example, an overprint food varnish in combination with a biologically active ligand is placed in contact with a dye conjugated to a peptide to form a homogeneous conjugate blend 124 as the peptide binds to the biologically active ligand. A single layer 116 in an icon shape of the homogeneous conjugate blend may be printed onto a flexible film 110. Thus, as in FIG. 12, a second layer introducing the peptide/dye conjugate is not required.

Figure 13B:
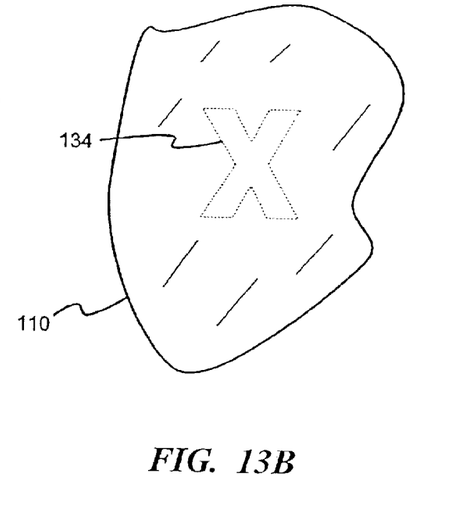
FIG. 13B illustrates a loss of visibility of an icon shape on a film.
Figure 15A:
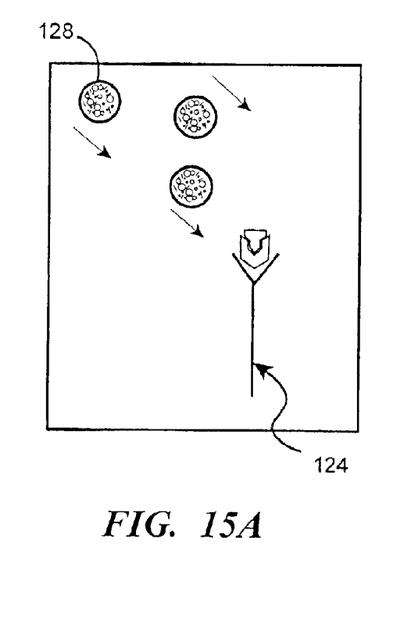
FIG. 15A demonstrates an antigen presented to a homogeneous conjugate blend.
Figure 15B:
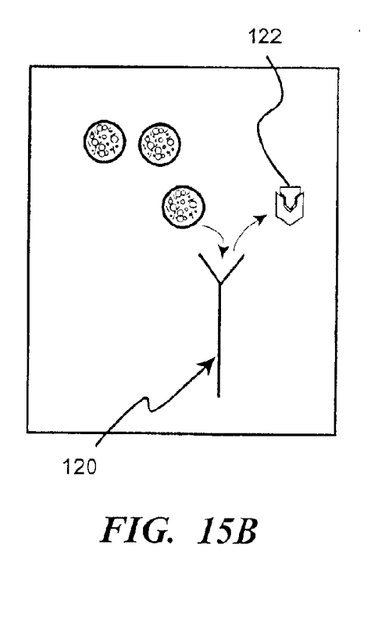
FIG. 15B demonstrates an antigen displacing a peptide/dye conjugate.
Figure 15C:
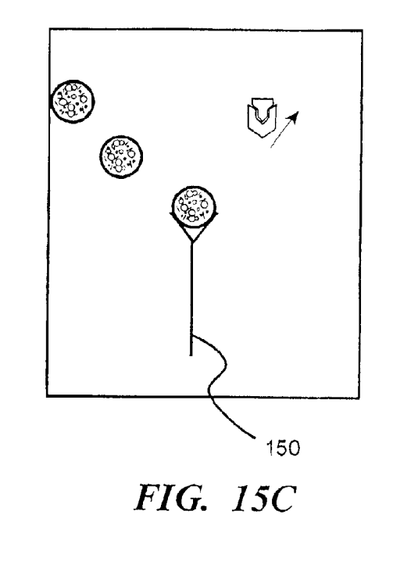
FIG. 15C demonstrates an antigen binding to an immobilized ligand.

The antigen, a particular toxic substance 128, being sought is competitive with the peptide conjugating the food dye for binding to the immobilized biologically active ligand. As illustrated in FIGS. 15A, 15B, and 15C, when the antigen 128 comes in contact with the biologically active ligand (FIG. 15A) having a degree of affinity for a particular toxic substance greater than that for the peptide, the antigen displaces the peptide, releasing the peptide/food dye conjugate 122 (FIG. 15B), thereby exhibiting loss of color within the icon "X" 134 (FIG. 13B). As the peptide/dye conjugate is displaced, the particular toxic substance binds to the immobilized ligand 150 (FIG. 15C) producing a visual signal, in this case loss of coloration within the "X", which is indicative of both the presence and identity of the particular toxic substance. So, when placing the flexible film in an environment which may contain a particular toxic substance, loss of coloration exhibited gives the user a visual cue to determine if the particular toxic substance is present. If no loss of color is exhibited, the particular toxic substance is absent. The user may also monitor the film for a period of time sufficient to observe a visual signal in order to determine the length of time necessary before the particular toxic substance reaches a level deemed unfit for consumption.

Figure 14A:
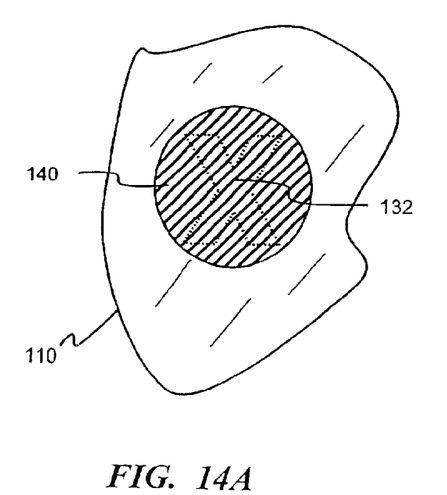
FIG. 14A illustrates a biological material assay in a first icon shape surrounded by a second icon shape on a film.
Figure 14B:
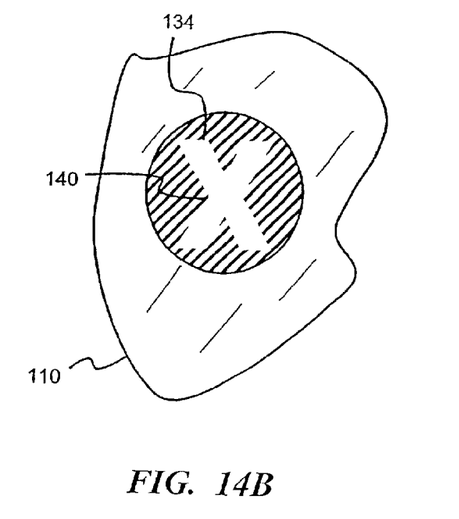
FIG. 14B illustrates a loss of visibility of a first icon shape on a film.

Alternatively, the parts needed to make a second icon shape, such as a circle 140 surrounding the "X" 132 to a sufficient degree as to render the first icon shape invisible, comprising the peptide conjugated food dye in a layer, may be printed directly onto a flexible polymer film 110. Referring to FIG. 14A, when surrounding the icon "X" 132 chosen with the same dye/peptide conjugate, the "X" is not visualized. Thus, when the antigen displaces the peptide and loss of color within the area of the "X" 134 occurs, the image will appear as a blue circle 140 with a white or colorless "X" 134 through or within it (FIG. 14B).

Any type of dye may be chosen that is approved for use with food products. In addition, more than one biologically active ligand may be utilized and more than one peptide may be utilized. Once the peptide/dye conjugate is allowed to bind to the immobilized ligand, the area may be washed to remove any excess conjugate not bound by the ligand. A liquid film may also be applied as a protectant layer covering the homogeneous conjugate blend. Also, when incorporating a second icon shape, a second dye may be utilized within the first icon shape, while still using a first dye, in order to create a visual signal in absence of a particular toxic substance and, in the presence of a particular toxic substance, create a visual color change within the first icon shape.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for detecting a presence of a particular toxic substance comprising:
   providing a liquid film in combination with a biologically active ligand, wherein said liquid has an ability to recognize an epitope of said toxic substance, and further has a degree of affinity for a peptide;
   providing a dye conjugated to said peptide;
   contacting said liquid film in combination with said biologically active ligand with said dye conjugated to said peptide to form a homogeneous conjugate blend having a particular coloration;
   applying said homogeneous conjugate blend to a surface of a flexible film whereby said homogeneous conjugate blend is immobilized thereon; and
   placing said flexible film in an environment which may contain said particular toxic substance;
   whereby upon contact with said particular toxic substance said substance competes with said peptide, resulting in a release of said peptide which exhibits a change in said particular coloration.

2. The process of claim 1, wherein said flexible film is a polyolefin or a polyvinylchloride.

3. The process of claim 2, wherein said polyolefin is selected from the group consisting of polyethylene, polypropylene and mixtures thereof.

4. The process of claim 1, wherein said surface of said flexible film has undergone a corona discharge treatment step effective to enhance said film's ability to immobilize a ligand applied thereto.

5. The process of claim 1, wherein said liquid film is an overprint food varnish.

6. A process for detecting a presence of a particular toxic substance comprising:
   providing a base layer which is a flexible film for immobilization of a biologically active ligand applied to a surface thereof, said ligand having an ability to recognize an epitope of said toxic substance, and further has a degree of affinity for a peptide;
   providing a first layer in an icon shape immobilized on said flexible film, wherein said first layer comprises a liquid film in combination with said biologically active ligand;
   providing a second layer in register with and bound to said first layer, wherein said second layer comprises a dye conjugated to said peptide which exhibits a particular coloration;
   placing said film in an environment which may contain said particular toxic substance, whereby upon contact with said particular toxic substance said substance competes with said peptide, resulting in a release of said peptide which exhibits a change in said particular coloration.

7. The process of claim 6, wherein said flexible film is a polyolefin or a polyvinylchloride.

8. The process of claim 7, wherein said polyolefin is selected from the group consisting of polyethylene, polypropylene and mixtures thereof.

9. The process of claim 6, wherein said surface of the flexible film has undergone a corona discharge treatment step effective to enhance said film's ability to immobilize a ligand applied thereto.

10. The process claim 6, wherein said liquid film is an overprint food varnish.

11. A process for detecting a presence of a particular toxic substance comprising;
    providing a homogeneous conjugate blend immobilized upon a film and having an icon shape and a particular coloration, wherein said homogeneous conjugate blend comprises a liquid film in combination with a biologically active ligand and a dye conjugated to a peptide, wherein said biologically active ligand has a degree of affinity for said particular toxic substance; and,
    contacting said homogeneous conjugate blend immobilized on said film with said particular toxic substance, wherein said biologically active ligand has a degree of affinity for said peptide which is lees than the degree of affinity for said particular toxic substance, and wherein said substance competes with said peptide, resulting in displacement of said peptide which results in a change in said particular coloration within said icon shape.

12. The process of claim 11, wherein said flexible film is a polyolefin or a polyvinylchloride.

13. The process of claim 12, wherein said polyolefin in is selected from the group consisting of polyethylene, polypropylene and mixtures thereof.

14. The process of claim 11, wherein said surface of said flexible film has undergone a corona discharge treatment step effective to enhance said film's ability to immobilize a ligand applied thereto.

15. The process of claim 11, wherein said liquid film is an overprint food varnish.

16. A process for detecting a presence of a particular toxic substance comprising:

providing a homogeneous conjugate blend immobilized upon a film and having an icon shape and particular coloration, wherein said homogeneous conjugate blend comprises a liquid film in combination with a biologically active ligand and a dye conjugated to a peptide, wherein said biologically active ligand has a degree of affinity for said particular toxic substance;

surrounding said homogeneous conjugate blend with said dye conjugated to said peptide in a circular shape; and, contacting said homogeneous conjugate blend immobilized on said film with said particular toxic substance, wherein said biologically active ligand has a degree of affinity for said peptide which is less than the degree of affinity for said particular toxic substance, and wherein said substance competes with said peptide, resulting in displacement of said peptide which results in a change in said particular coloration within said icon shape.

17. The process of claim 16, wherein said flexible film is a polyolefin or a polyvinylchloride.

18. The process of claim 17, wherein said polyolefin is selected from the group consisting of polyethylene, polypropylene and mixtures thereof.

19. The process of claim 16, wherein said surface of said flexible film has undergone a corona discharge a treatment step effective to enhance said film's ability to immobilize a ligand applied thereto.

20. The process of claim 16, wherein said liquid film is an overprint food varnish.

* * * * *